United States Patent [19]

Wendelbo

[11] Patent Number: 5,609,843
[45] Date of Patent: Mar. 11, 1997

[54] MICROPOROUS CRYSTALLINE SILICO-ALUMINO-PHOSPHATE AND A PROCEDURE FOR MANUFACTURING IT

[75] Inventor: Rune Wendelbo, Oslo, Norway

[73] Assignee: Norsk Hydro a.s, Oslo, Norway

[21] Appl. No.: 591,657

[22] PCT Filed: Jul. 22, 1994

[86] PCT No.: PCT/NO94/00130

§ 371 Date: Feb. 12, 1996

§ 102(e) Date: Feb. 12, 1996

[87] PCT Pub. No.: WO95/05342

PCT Pub. Date: Feb. 23, 1995

[30] Foreign Application Priority Data

Aug. 17, 1993 [NO] Norway .................................. 932915

[51] Int. Cl.$^6$ .................................................. C01B 25/36
[52] U.S. Cl. ...................... 423/306; 423/327.1; 502/214; 518/728
[58] Field of Search .................... 518/728; 423/306; 502/214

[56] References Cited

U.S. PATENT DOCUMENTS

| 4,310,440 | 1/1982 | Wilson et al. | 252/435 |
| 4,440,871 | 4/1984 | Lok et al. | 502/214 |

FOREIGN PATENT DOCUMENTS

WO93/13013  7/1993  WIPO .

*Primary Examiner*—Gary Geist
*Assistant Examiner*—Sreeni Padmanabhan
*Attorney, Agent, or Firm*—Wenderoth, Lind & Ponack

[57] ABSTRACT

A microporous crystalline silico-alumino-phosphate RUW-18, the theoretical composition of which, on a water-free basis after synthesis and calcination, is: $H_xSi_xAl_yP_zO_2$ where x has a value between 0.005 and 0.1 and y and z are values between 0.4 and 0.6. The product has an AEI structure and possesses acidic properties. A procedure for manufacturing the product is also described. RUW-18 is suitable as a sorbent and as a catalyst in the manufacture of olefins from methanol.

12 Claims, No Drawings

MICROPOROUS CRYSTALLINE SILICO-ALUMINO-PHOSPHATE AND A PROCEDURE FOR MANUFACTURING IT

The present invention concerns a crystalline silico-alumino-phosphate (SAPO) with an AEI structure, which has acidic properties, and a procedure for manufacturing it. The present invention particularly concerns the manufacture of the new silico-alumino-phosphate RUW-18.

Microporous crystalline silico-alumino-phosphates and a procedure for manufacturing such products are, for example, mentioned in Norwegian patent no. 169380. These products have a three-dimensional crystal lattice built up of $PO_2+$, $AlO_2$-tetrahedron units in which $SiO_2$ tetrahedron units are substituted for $PO_2+$ and the empirical chemical composition of which, on a water-free basis, is:

$$mR: (Si_xAl_yP_z) O_2$$

where R means at least one organic template material which is present in the intercrystalline pore system and m means the number of mol R which are present per mol $(Si_xAl_yP_z) O_2$ and has a value from 0 to 0.3. The sum of x, y and z equals 1, and the minimum value for "x" is 0.005, the minimum value for "y" and "z" is 0.01, and the maximum value for "x" is 0.98, for "y" 0.6 and for "z" 0.52.

Reaction mixtures for silico-alumino-phosphate are made by combining at least a proportion of each of the aluminium and phosphorus sources with water, where the silicon source is mainly absent. Subsequently, the resulting mixture reacts with a silicon source and then with an organic compound. The mixing sequence is critical only in some cases.

The reaction mixture is placed in a pressure container for heating under autogenous pressure to a temperature of at least 100° C., preferably between 100° and 260° C., until a crystalline silico-alumino-phosphate is obtained. The solid substance is recovered in any appropriate way, for example by centrifuging or filtering. The recovered substance is dried and calcinated in the presence of air.

During calcination the organic template material R will be combusted and in those cases where it occurs as a charge-compensating cation, there will be an $H^+$ ion left behind as a new charge-compensating ion. This will be the case for silico-alumino-phosphates, which will thus gain acidic properties after calcination.

Of the known silico-alumino-phosphates, molecular sieves with a three-dimensional pore structure with 8-ring pores will be the most interesting for gas separation and the production of olefins from methanol. SAPO-34 and SAPO-17 can be mentioned as known silico-alumino-phosphates (SAPO) with this structure.

The AEI structure is described by Simmen et al., 1991: Zeolites 11, 654. This structure has a three-dimensional pore network with pore openings of approximately 4–5 Å and with cavities, the smallest dimensions of which are >5 Å. The crystals are usually plate-shaped. The effective diameter of the crystallite is small and there will be a short diffusion path into the centre of the crystallite. Silico-alumino-phosphates with an AEI structure have not previously been known.

Crystalline alumino-phosphates with an AEI structure have previously been produced (U.S. Pat. No. 4,310,440), but they do not possess acidic properties because the crystal lattice is electrically neutral. They cannot, therefore, be used as catalysts in reactions where acidity is required, for example for converting methanol to olefins. The properties as a sorbent will also be different for molecular sieves with and without acidic properties. An acidic molecular sieve will be polarised and thus have greater sorption capacity.

The object of the present invention is to manufacture a crystalline silico-alumino-phosphate with acidic properties and with a pore structure which is made of channels with a diameter between 4 and 5 Å and with "cavities", the smallest size of which is >5 Å. Another object is to manufacture a material which can be used as catalysts or sorbents in a wide range of contexts, for example for the manufacture of olefins from methanol.

These and other objects of the present invention are achieved with the product and the procedure described below and the present invention is defined and characterised by the patent claims.

The present invention concerns a microporous crystalline silico-alumino-phosphate, the theoretical chemical composition of which, on a water-free basis after synthesis and calcination, is:

$$H_xSi_xAl_yP_zO_2$$

where x has a value between 0.005 and 0.1 and y and z are values between 0.4 and 0.6, and "x", "y" and "z" are mol fractions of silicon, aluminium and phosphorus respectively, present as tetrahedric oxides.

The manufactured molecular sieve RUW-18 consists of plate-shaped crystals which, after calcination in air at 550° C. for 4 hours, produce a characteristic X-ray diffractogram which at least includes the reflexes stated in table 1 and no very strong, strong or medium strong reflexes apart from those stated in area 2 theta<24. This is identical to an AEI structure.

TABLE 1

| 2θ | d | 100 × I/I₀ |
|---|---|---|
| 9.4–9.5 | 9.31–9.41 | vs |
| 10.5–10.6 | 8.35–8.43 | w |
| 12.8–12.9 | 6.86–6.92 | w |
| 13.4–13.5 | 6.56–6.61 | w |
| 16.0–16.1 | 5.51–5.54 | w |
| 16.8–16.9 | 5.25–5.28 | m |
| 17.1–17.2 | 5.16–5.19 | m |
| 19.0–19.1 | 4.65–4.67 | w |
| 19.6–19.7 | 4.51–4.53 | w |
| 19.9–20.0 | 4.44–4.46 | w |
| 20.6–20.7 | 4.29–4.31 | m |
| 21.3–21.4 | 4.15–4.17 | m |
| 21.7–21.8 | 4.08–4.10 | w |
| 21.9–22.0 | 4.04–4.06 | w |
| 22.3–22.5 | 3.95–3.99 | w |
| 23.8–23.9 | 3.72–3.74 | w | vs = 90–100
m = 20–70
w = 5–19

The product has acidic properties as demonstrated by the fact that >0.1 mmol $NH_3$/g material sorbed at room temperature is desorbed again at temperatures >300° C. with a local desorption maximum which is above 350° C. when it is heated in flowing helium at a speed of 10° C./min.

The content of Si in the calcinated product is in the range between 0.2 and 3% weight, preferably between 0.4 and 1.2. The manufactured product has an AEI structure with channels of 4–5 Å diameter and with cavities, the smallest size of which is >5 Å.

RUW-18 is manufactured from a mixture of reactive sources of $SiO_2$, $Al_2O_3$ and $P_2O_5$ and an organic template material. The mixture is manufactured by combining at least one portion of the Al source and the P source in the absence of the Si source and subsequently mixing the resulting mixture with the other ingredients. Finally, the product is dried and calcinated. It was discovered, surprisingly, that it was important to add water and phosphoric acid separately to the synthetic mixture to manufacture RUW-18. Part of the liquid phase has to be removed before the organic template is added, for example by filtering or evaporation. 20–50% of the entire weight of the gel can be removed. However, it is preferable to remove 35–45%. The reaction mixture must then be heated up to over 100° C., preferably to 180°–260° C., and must be kept at this temperature for at least 4 hours to obtain a reasonable yield. A lower temperature will require more time. The content of $SiO_2$ in the gel must be kept below 5% weight.

The RUW-18 crystals are plate-shaped and their size varies greatly. The plate shape seems to be typical for the AEI structure. The product is suitable both as a catalyst for the manufacture of olefins from methanol and as a sorbent.

Acidic sites on the molecular sieves can be demonstrated, for example with temperature-programmed desorption (TPD) of $NH_3$. Depending on the test conditions, the catalytically active acidic sites will be shown as a peak in a TPD profile between approximately 350° C. and 500° C., while peaks between 150° C. and 250° C., on the other hand, represent physically sorbed $NH_3$ and not very acidic sites.

In the manufacture of silico-alumino-phosphates the choice of sources of aluminium oxide, silica and phosphorus pentoxide is not critical. For example, aluminium isopropoxide, phosphoric acid and silicasol can be used. Tetraethyl ammonium hydroxide solution (TEAOH), cyclopentylamine, aminomethyl-cyclohexane, piperidine, cyclohexylamine and triethyl-hydroxyethylamine are examples of suitable template materials.

The present invention is to be illustrated in further detail by means of the following examples. These examples must not be perceived as being the only methods for manufacturing RUW-18.

EXAMPLE 1

A reaction mixture was manufactured by mixing 108 g of distilled water with 81.6 g of aluminium isopropoxide with subsequent shaking for one minute. 45 g 85% phosphoric acid was added and the mixture was shaken for a further minute while being cooled. Then 0.6 g 37% HCl was added and the mixture was shaken again for one minute while being cooled. 3.0 g Ludox LS colloidal silica (30% $SiO_2$, 70% water) was added to the mixture before it was shaken again while being cooled. After standing for 15 minutes, the mixture was filtered and 89 g of the liquid was filtered off (37%). The filter cake was replaced in the bottle and 49 g 40% TEAOH was added. After being shaken for one minute and being left to stand for half an hour, the contents were divided up into three portions. 32.6 g 40% TEAOH was added to one of the portions and the mixture was shaken for one minute. The mixtures were subsequently transferred to an autoclave on a shaking table overnight at room temperature. Then the temperature was increased to 215° C. and the mixtures were kept at this temperature for 120 hours. After cooling, the product was washed with distilled water and centrifuged. It was subsequently calcinated in dry air at 550° C. for 5 hours.

The X-ray diffractogram which is characteristic for the new RUW-18 silico-alumino-phosphate is shown in table 2. The sample contained only insignificant quantities of crystalline impurities.

TABLE 2

| 2θ | d | 100 × I/I$_o$ |
|---|---|---|
| 7.39* | 11.96 | 4 |
| 9.48 | 9.33 | 100 |
| 10.58 | 8.36 | 10 |
| 12.88 | 6.87 | 13 |
| 13.44 | 6.59 | 3 |
| 13.93 | 6.36 | 2 |
| 16.04 | 5.52 | 9 |
| 16.89 | 5.25 | 9 |
| 17.18 | 5.16 | 9 |
| 19.05 | 4.66 | 3 |
| 19.63 | 4.52 | 3 |
| 19.99 | 4.44 | 4 |
| 20.63 | 4.31 | 13 |
| 21.31 | 4.17 | 7 |
| 21.94 | 4.05 | 1 |
| 22.40 | 3.97 | 2 |
| 23.11 | 3.85 | 2 |
| 23.89 | 3.72 | 7 |

*Peaks which are assumed to represent crystalline impurities.

The composition of the solid, calcinated product was established, by means of chemical analysis, as 38.2% $Al_2O_3$, 1.72% $SiO_2$, 60.5% $P_2O_5$ which produced a product composition, with regard to the main components, of $Si_{0.02}Al_{0.46}P_{0.52}O_2$.

The acidity of the RUW-18 was measured with temperature-programmed desorption of $NH_3$ on an AMI-1 from Altamira Instruments. The measurements showed two different peaks with maxima at 181° C. and 407° C. respectively, and a local maximum of 288° C. The measurements also showed that 0.4 mmol $NH_3$ was desorbed per g of dry sample in the temperature range 288°–550° C., and it can be assumed that the greater part of this quantity of $NH_3$ represents very acidic sites.

EXAMPLE 2

A reaction mixture as described in example 1, but without added HCl, was manufactured. This time it was filtered from 100 g liquid (41%), and the filter cake was subsequently divided into 3 equal parts before TEAOH was added. Then 49 g 40% TEAOH solution was added to one of these three parts, and the whole mixture was shaken for one minute and then placed in an autoclave. Further processing was as described in example 1 apart from the heat treatment being carried out for 170 hours instead of for 120 hours.

Synthesised and calcinated (dry air, 550° C., 5 hours), the product had an X-ray diffractogram characterised by data as shown in table 3.

TABLE 3

| 2θ | d | 100 × I/I$_o$ |
|---|---|---|
| 9.49 | 9.32 | 100 |
| 10.57 | 8.37 | 13 |
| 12.90 | 6.86 | 10 |
| 13.41 | 6.60 | 5 |
| 16.05 | 5.52 | 9 |
| 16.87 | 5.25 | 13 |
| 17.15 | 5.17 | 13 |
| 19.04 | 4.66 | 4 |
| 19.64 | 4.52 | 3 |
| 19.98 | 4.44 | 5 |
| 20.65 | 4.30 | 10 |
| 21.31 | 4.17 | 8 |

TABLE 3-continued

| 2θ | d | 100 × I/I₀ |
|---|---|---|
| 21.90 | 4.06 | 1 |
| 22.42 | 3.97 | 1 |
| 22.84 | 3.89 | 2 |
| 23.13* | 3.85 | 2 |
| 23.87 | 3.73 | 9 |
| 25.15 | 3.54 | 3 |
| 26.00 | 3.43 | 4 |
| 26.23 | 3.40 | 5 |
| 27.79 | 3.21 | 5 |
| 29.07 | 3.07 | 2 |
| 30.01 | 2.98 | 3 |
| 30.39 | 2.94 | 5 |
| 31.12 | 2.87 | 8 |
| 31.56 | 2.83 | 3 |
| 32.13 | 2.79 | 5 |
| 32.68 | 2.74 | 3 |
| 33.78 | 2.65 | 2 |
| 34.78 | 2.58 | 2 |
| 36.54 | 2.46 | 1 |
| 43.19 | 2.09 | 1 |
| 44.29* | 2.05 | 1 |
| 48.97 | 1.86 | 2 |
| 55.31 | 1.66 | 2 |
| 55.90 | 1.64 | 2 |

*Reflexes which are assumed to represent crystalline impurities.

The composition of the calcinated product was established, by means of chemical analysis, as being 37.5% $Al_2O_3$, 1.79% $SiO_2$, 61.5% $P_2O_5$ The $NH_3$ TPD measurement showed two clear separate peaks with maxima at 185° C. and 424° C. respectively, and a local minimum at about 303° C. The measurement also showed that 0.4 mmol $NH_3$ was desorbed per g dry sample in the temperature range 303°–550° C. and it is assumed that the greater part of this quantity of $NH_3$ represents very acidic sites.

EXAMPLE 3

As a comparative example, a sample of ALPO-18 was manufactured by using the same recipe as in example 2 without the addition of silicon. The calcinated product contained the characteristic X-ray reflexes as stated in U.S. Pat. No. 4,310,440, example 46 b, and, in addition, some reflexes which showed a content of <10% ALPO-5. The $NH_3$ TPD measurement showed only one peak in the TPD profile with a maximum at 180° C. and that only 0.05 mmol $NH_3$ was desorbed per g dry sample in the temperature range 297°–550° C.

EXAMPLE 4

A test was carried out to convert methanol into light olefins. A sample of the calcinated material described in example 1 was compressed into tablets. The tablets were then carefully crushed and a 35–70 mesh fraction was removed by screening. 0.5 g of this powder was placed in a reactor of stainless steel and a mixture of 40% methanol and 60% nitrogen was passed through it at a speed of 0.5 g of methanol per hour at a temperature of 420° C.

The products were analysed by gas chromatography and the composition after 325 minutes was as shown in table 4.

TABLE 4

| Content % weight | Product |
|---|---|
| 42.3 | ethylene |
| 42.4 | propene |
| 12.8 | butenes |
| 1.5 | methane |
| 0.6 | ethane |
| 0.0 | propane |
| 0.2 | butanes |
| 0.3 | $C_{5+}$ |

The result shows that the RUW-18 manufactured is a good catalyst for the conversion of methanol into light olefins.

EXAMPLE 5

A sample of the same material as that manufactured in example 2 was tested for separation of normal alkanes from isoalkanes. 2.75 g of the material was placed in a Schlenk tube and flushed with nitrogen. Normal butane was subsequently passed through the sample at approximately 60 ml/min for 15 minutes. After this the weight of the sample had increased by 12% to 3.09 g.

The test was then also carried out with sorption of isobutane. 3.40 g of the material manufactured in accordance with example 2 was placed in a Schlenk tube and flushed with nitrogen, 60 ml/min isobutane was then passed through the tube for 15 minutes, After this treatment the weight of the sample had increased by 0.6% to 3.42 g.

The results show that the RUW-18 manufactured can be used for separating isoalkanes and n-alkanes, in particular butanes, by normal alkane being sorbed into the pores of the molecular sieve, whereas the isoalkane cannot be sorbed because its kinetic diameter is too large. RUW-18 can probably also be used to separate heavier isoalkanes and n-alkanes and alkenes.

I claim:

1. A microporous crystalline silico-alumino-phosphate, the theoretical composition of which, on a water-free basis after synthesis and calcination, is:

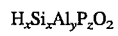

$H_xSi_xAl_yP_zO_2$ where x has a value between 0.005 and 0.1 and y and z are values between 0.4 and 0.6, characterised in that the product, after calcination in air at 550° C. for 4 hours, produces a characteristic X-ray diffractogram as shown in table 1

TABLE 1

| 2θ | d | 100 × I/I₀ |
|---|---|---|
| 9.4–9.5 | 9.31–9.41 | vs |
| 10.5–10.6 | 8.35–8.43 | w |
| 12.8–12.9 | 6.86–6.92 | w |
| 13.4–13.5 | 6.56–6.61 | w |
| 16.0–16.1 | 5.51–5.54 | w |
| 16.8–16.9 | 5.25–5.28 | m |
| 17.1–17.2 | 5.16–5.19 | m |
| 19.0–19.1 | 4.65–4.67 | w |
| 19.6–19.7 | 4.51–4.53 | w |
| 19.9–20.0 | 4.44–4.46 | w |
| 20.6–20.7 | 4.29–4.31 | m |
| 21.3–21.4 | 4.15–4.17 | m |

TABLE 1-continued

| 2θ | d | 100 × I/I$_o$ |
|---|---|---|
| 21.7–21.8 | 4.08–4.10 | w |
| 21.9–22.0 | 4.04–4.06 | w |
| 22.3–22.5 | 3.95–3.99 | w |
| 23.8–23.9 | 3.72–3.74 | w | vs = 90–100
m = 20–70
w = 5–19

2. A silico-alumino-phosphate in accordance with claim 1, characterised in that it has acidic properties as demonstrated by the fact that >0.1 mmol NH$_3$/g of material sorbed at room temperature is desorbed again at temperatures >300° C. with a local desorption maximum which is above 350° C. when it is heated in flowing helium at a speed of 10° C./min.

3. A silico-alumino-phosphate in accordance with claim 1, characterised in that it contains 0.2–3% by weight SiO$_2$.

4. A silico-alumino-phosphate in accordance with claim 1, characterised in that it has an AEI structure with channels of 4–5 Å diameter and cavities, the smallest size of which is >5 Å.

5. A procedure for manufacturing silico-alumino-phosphates with an AEI structure from a mixture of reactive sources of SiO$_2$, Al$_2$O$_3$ and P$_2$O$_5$ and an organic template material, in which the mixture is manufactured by combining at least one portion of the Al source and the P source in the absence of the Si source and then mixing the resulting mixture with the other ingredients, followed by drying and calcination, characterised in that the aluminium source is mixed with water before the phosphorus source is added and in which, after adding the Si source, a significant part of the liquid phase is removed from the resulting gel before the template material is added.

6. A procedure in accordance with claim 5, characterised in that 20–50% of the liquid phase is removed.

7. A procedure in accordance with claim 5, characterised in that dehydration is carried out by filtering or drying.

8. A procedure in accordance with claim 5, characterised in that the content of SiO$_2$ in the gel is kept below 5% weight.

9. A silico-alumino-phosphate in accordance with claim 3, which contains 0.4–1.2% by weight SiO$_2$.

10. A procedure in accordance with claim 6, wherein 35–45% of the liquid phase is removed.

11. In a process which comprises producing olefins from methanol in the presence of a catalyst, the improvement wherein the catalyst is a microporous crystalline silico-alumino-phosphate in accordance with claim 1.

12. In a process which comprises sorbing a material by means of a molecular sieve, the improvement wherein the molecular sieve is a microporous crystalline silico-alumino-phosphate in accordance with claim 1.

* * * * *